United States Patent [19]

Marker et al.

[11] Patent Number: 4,855,110
[45] Date of Patent: Aug. 8, 1989

[54] SAMPLE RING FOR CLINICAL ANALYZER NETWORK

[75] Inventors: Edwin M. Marker, Chicago; Paul F. Thacker, Wauconda; Peter K. Knopfhart, Libertyville, all of Ill.

[73] Assignee: Abbott Laboratories, North Chicago, Ill.

[21] Appl. No.: 46,964

[22] Filed: May 6, 1987

[51] Int. Cl.$^4$ .................. G01N 35/02; B01L 3/00; B01L 9/00

[52] U.S. Cl. .................. 422/102; 422/64; 422/104; 211/74

[58] Field of Search .................. 422/63-67, 422/72, 73, 100, 99; 3/102, 104; 211/74

[56] References Cited

U.S. PATENT DOCUMENTS

| | | | |
|---|---|---|---|
| 2,808,581 | 10/1957 | Findlay | 340/244 |
| 3,190,731 | 6/1965 | Weiskopf | 23/292 |
| 3,219,416 | 11/1965 | Natelson | 422/64 |
| 3,266,322 | 8/1966 | Negersmith | 422/64 |
| 3,565,582 | 2/1971 | Young | 23/230 |
| 3,612,321 | 10/1971 | Larson | 422/102 |
| 3,615,236 | 10/1971 | Tamm | 23/253 |
| 3,623,844 | 11/1971 | Anthon | 422/64 |
| 3,680,967 | 8/1972 | Engelhardt | 422/64 |
| 3,756,920 | 9/1973 | Kelbaugh et al. | 195/127 |
| 3,764,268 | 10/1973 | Kosowsky et al. | 422/64 |
| 3,787,185 | 1/1974 | Rohrbaugh et al. | 23/253 |
| 3,801,283 | 4/1974 | Shapiro | 422/64 |
| 3,854,508 | 12/1974 | Burtis et al. | 141/130 |
| 3,883,308 | 5/1975 | Matte | 23/259 |
| 3,942,952 | 3/1976 | Atwood | 422/64 |
| 3,951,605 | 4/1976 | Natelson | 23/253 |
| 3,963,349 | 6/1976 | Albright et al. | 73/64.1 |
| 3,969,079 | 7/1976 | Catarious et al. | 23/253 |
| 3,994,171 | 11/1976 | Schwartz | 73/423 |
| 4,126,418 | 11/1978 | Krasnow | 422/64 |
| 4,141,954 | 2/1979 | Shigetomi | 422/64 |
| 4,158,545 | 6/1979 | Yamashita et al. | 23/230 |
| 4,225,558 | 9/1980 | Peterson et al. | 422/72 |
| 4,234,539 | 11/1980 | Ginsberg et al. | 422/64 |
| 4,235,840 | 11/1980 | Mendoza et al. | 422/64 |
| 4,267,149 | 5/1981 | Bruckner et al. | 422/65 |
| 4,271,123 | 6/1981 | Curry et al. | 422/64 |
| 4,286,637 | 9/1981 | Wilson | 422/102 |
| 4,287,155 | 9/1981 | Tersteeg et al. | 422/64 |
| 4,309,384 | 1/1982 | Trod | 422/64 |
| 4,310,488 | 1/1982 | Rahm et al. | 422/102 |
| 4,314,970 | 2/1982 | Stein et al. | 422/64 |
| 4,326,851 | 4/1982 | Bello et al. | 23/230 |
| 4,338,279 | 7/1982 | Orimo et al. | 422/64 |
| 4,341,736 | 7/1982 | Drbal et al. | 422/100 |
| 4,344,768 | 8/1982 | Parker et al. | 23/230 |
| 4,357,301 | 11/1982 | Cassaday et al. | 422/64 |
| 4,360,360 | 11/1982 | Chiknas | 23/230 |
| 4,383,041 | 5/1983 | Kutsusawa et al. | 435/291 |
| 4,451,433 | 5/1984 | Yamashita et al. | 422/63 |
| 4,456,370 | 6/1984 | Kondo et al. | 356/418 |
| 4,459,265 | 7/1984 | Berglund | 422/64 |
| 4,469,793 | 9/1984 | Guigan | 436/45 |
| 4,477,578 | 10/1984 | Miles et al. | 436/518 |
| 4,517,160 | 5/1985 | Galle et al. | 422/65 |
| 4,517,850 | 5/1985 | Wiseman et al. | 73/864.21 |
| 4,528,159 | 7/1985 | Liston | 422/65 |
| 4,540,549 | 9/1985 | Manabe | 422/64 |
| 4,543,238 | 9/1985 | Mimura et al. | 422/63 |
| 4,598,596 | 7/1986 | Wiseman et al. | 73/864.22 |
| 4,608,231 | 8/1986 | Witty et al. | 422/61 |
| 4,678,752 | 7/1987 | Thorne et al. | 435/291 |

Primary Examiner—Michael S. Marcus
Attorney, Agent, or Firm—Roberta L. Hastreiter

[57] ABSTRACT

A sample containment apparatus for use in an automated analyzer network is disclosed. The sample containment apparatus comprises a ring and a plurality of sample containers attached or mounted thereto. Each sample container has the capacity to contain an aliquot of sample sufficient for an entire battery of tests to be performed. Mounting flanges are disclosed for removably mounting the sample containment apparatus on carousels of each of a selected plurality of analyzers in the network to perform a selected plurality of tests on the samples.

20 Claims, 5 Drawing Sheets

FIG. 2
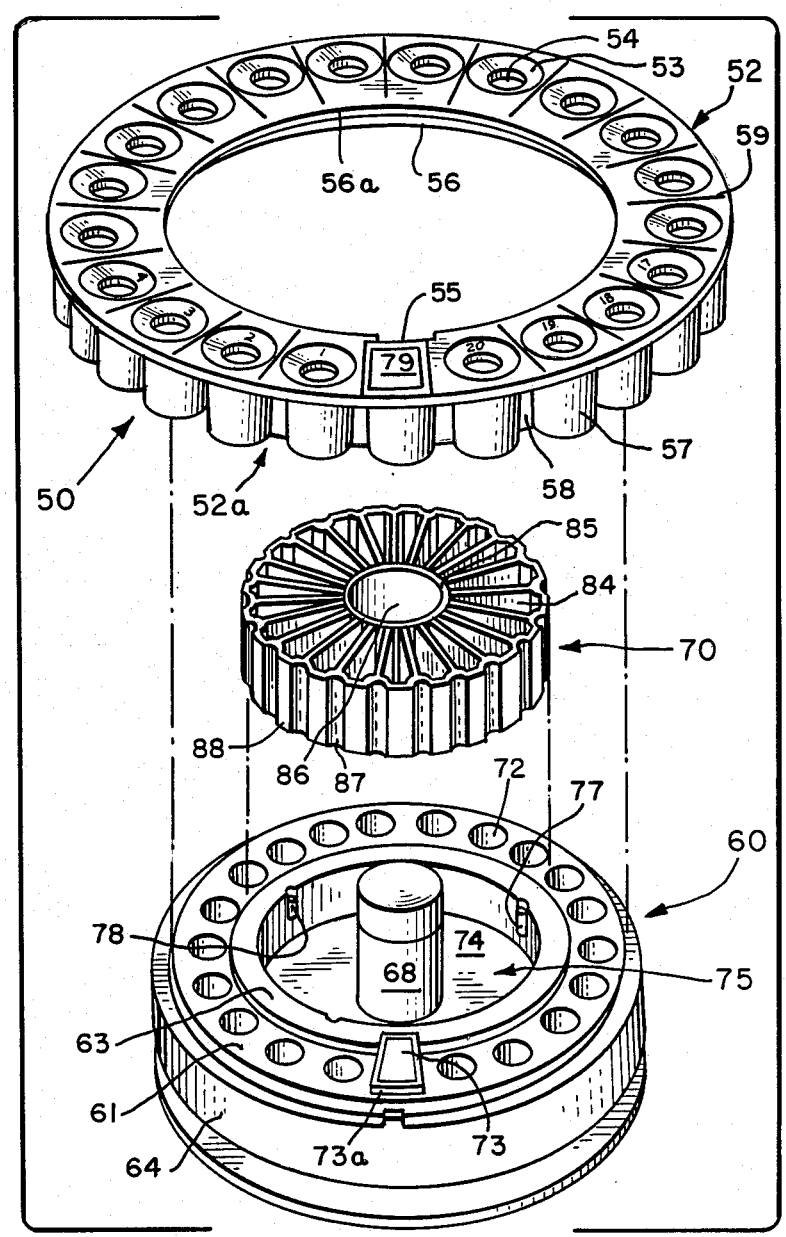
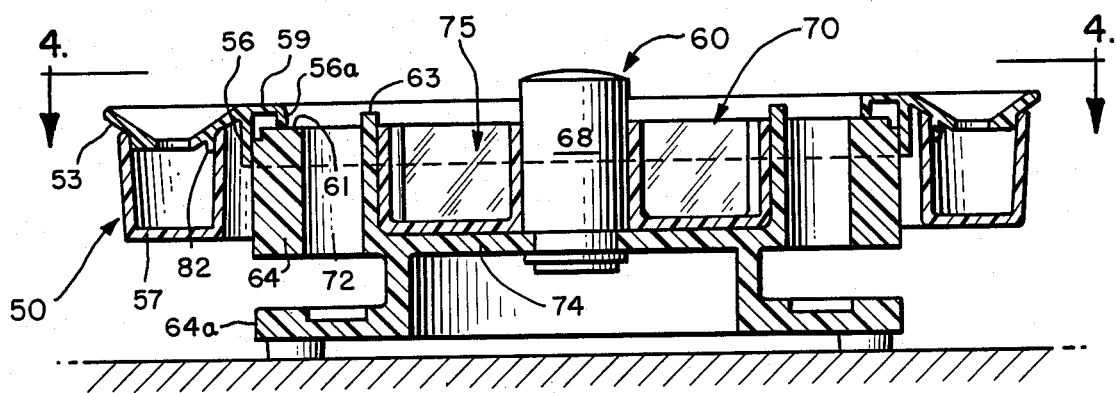
FIG. 3

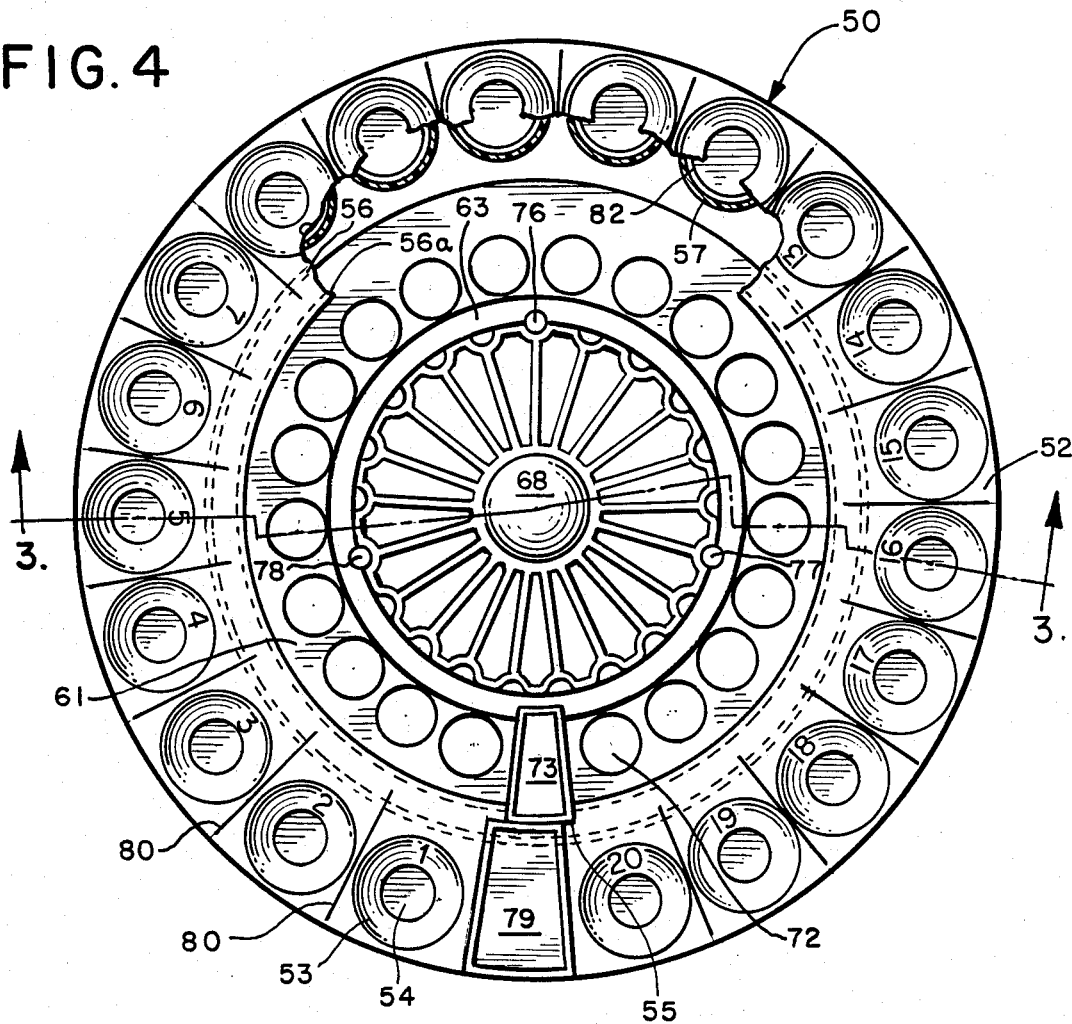
FIG. 4
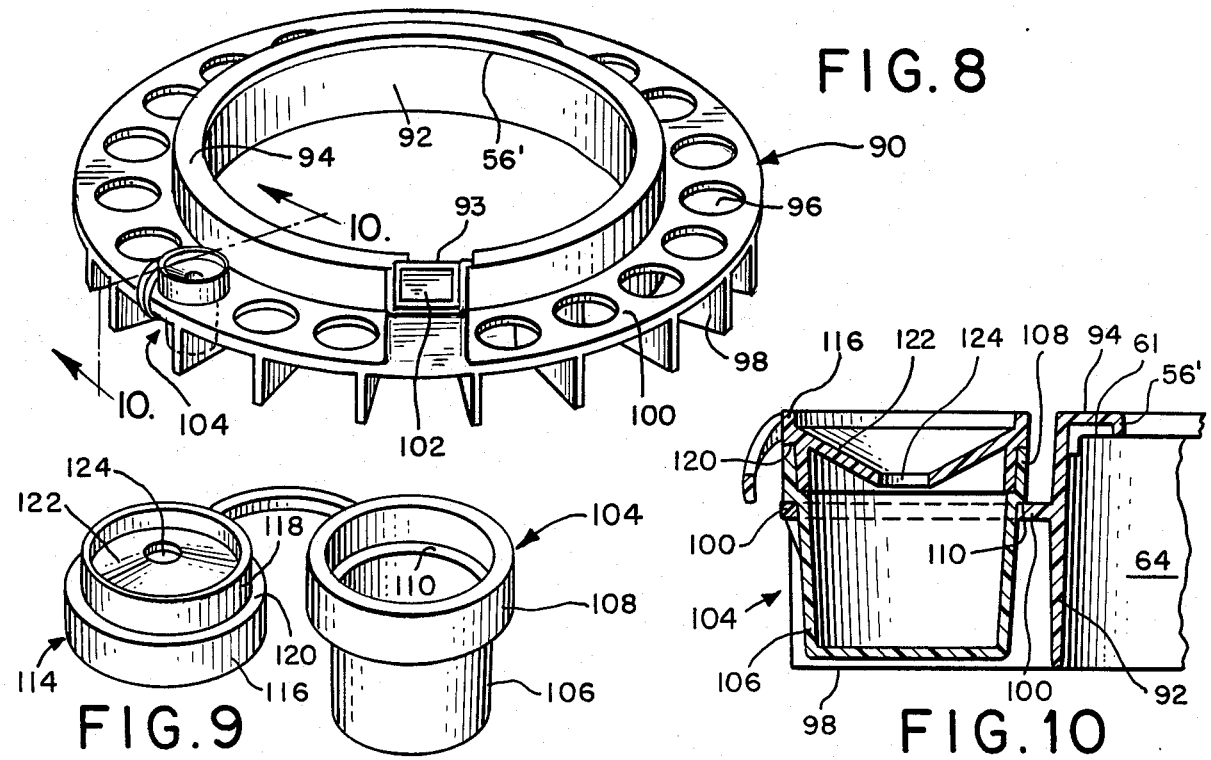
FIG. 8
FIG. 9
FIG. 10

SAMPLE RING FOR CLINICAL ANALYZER NETWORK

BACKGROUND OF THE INVENTION

1. Field of the Invention

This invention relates generally to sample containers for use in automated clinical analyzers which are operative to test various biological samples for the presence of drugs, viruses, and other analytes. More specifically, the invention relates to a sample containment apparatus which is capable of holding a plurality of samples and which is adapted to be expeditiously mounted sequentially on carousels of a selected plurality of optimized clinical analyzers which are networked to perform a selected battery of tests on each of the plurality of samples.

2. Description of the Related Art

Automated clinical analyzers which operate under program control to automatically analyze batches of biological samples for various analytes such as drugs, viruses, and the like are known in the art. An example of such an automated analyzer is the TDx ® clinical analyzer which is manufactured and sold by Abbott Laboratories of North Chicago, Ill. The TDx ® and other such clinical analyzers are generally capable of analyzing a batch of biological samples such as serum, urine, and the like for multiple selected analytes, such as those mentioned above, one analyte or group of related analytes at a time. With such analyzers, if it is necessary or desirable to test the same biological sample for more than one analyte, such as when testing for the usage of a number of selected illegal drugs is being conducted, each test must be carried out sequentially. Typically between tests, such analyzers must be set up with new reagents, new samples must be loaded, and instructions for the new test loaded or entered. If multiple batches of different samples are to be tested, this time-consuming procedure must be performed for each test of each batch. As a result, such machines standing alone generally are not practical or effective in applications which require relatively rapid high volume testing of samples for multiple analytes.

The throughput limitations associated with such standalone analyzers are largely overcome by interconnecting a plurality of such analyzers in a network in which each analyzer is set up and optimized to test a group of samples for a specific selected analyte or group of analytes. In a network for performing drug testing, for example, one analyzer can be testing one group of samples for cocaine at the same time a second analyzer is testing a second group for marijuana, and a third analyzer is testing a third group for amphetamines. Each group of samples may be sequentially tested by each analyzer until each sample has been tested for all of the analytes of interest. Alternatively, multiple duplicate groups of the same samples may be tested by each analyzer simultaneously.

In order to maximize the throughput of such a network, it is desirable to minimize both the sample preparation time and the time between tests. With existing sample containment apparatus, it is necessary to individually prepare multiple duplicate groups of sample containers with samples for each individual test to be simultaneously performed or to refill or fill new sample containers for each sequential test. This requirement is time consuming, adversely impacts system throughput, and increases the risk of sample contamination.

Thus, there is a need for sample containment means which provides expedient, rapid, and safe preparation and transportation of a plurality of samples between the various analyzers of a network with minimal risk of contamination. There is also a need for such means that can be used with existing carousel-type delivery means. A desirable feature of such means is the provision of individual sample containers each having the capability to hold an aliquot of sample sufficient to supply an adequate volume of sample for testing by multiple analyzers. Another desirable feature is the provision of means to minimize the possibility of contamination of samples during preparation, testing, and transportation operations. Still another desirable feature is the provision of means to promote flexibility and expediency in filling individual sample containers. The present invention has as its primary object to satisfy the foregoing needs by providing a sample containment means especially adapted for use in an automated analyzer network of the type described and having the foregoing and other features and advantages.

SUMMARY OF THE INVENTION

The invention satisfies the foregoing needs and achieves the foregoing features and advantages by providing a sample containment apparatus comprising a ring having a plurality of openings for receiving samples. A plurality of sample containers each having sufficient capacity to contain a volume of sample adequate for testing by a selected plurality of analyzers is attached to the ring beneath said openings to form a fluid-tight connection. The ring is provided with mounting means for removably mounting the sample containment apparatus on each carousel of a selected plurality of analyzers for performing a selected plurality of tests on the samples.

BRIEF DESCRIPTION OF THE DRAWING

The elements which are believed to characterize the invention are set forth in the appended claims. The invention itself together with the foregoing objects, features, and advantages thereof, and others, will be best understood by reference to the following detailed description taken in conjunction with the drawings, in which:

FIG. 2 is an exploded front perspective view of a first preferred embodiment of the sample containment ring together with a typical analyzer carousel and diluent-containing ring;

FIG. 3 is a front elevation view in section of the first preferred embodiment of the sample containment ring shown mounted, together with the diluent-containing ring, on the analyzer carousel as shown in FIG. 4, taken along a line 3—3;

FIG. 4 is a partially exposed top plan view of the first preferred embodiment of the sample containment ring shown mounted, together with the diluent-containing ring, on the analyzer carousel as shown in FIG. 3, taken along a line 4—4;

FIG. 8 is a front perspective view of a second preferred embodiment of the sample containment ring of the invention with a representative removable sample container and lid mounted therein;

FIG. 9 is a perspective view of a representative sample container and lid adapted for use with the sample containment ring of FIG. 8 showing the lid removed from the sample container;

FIG. 10 is a side elevation view in section of the sample container and lid of FIG. 8 taken along a line 10—10.

DETAILED DESCRIPTION OF THE PRESENTLY PREFERRED EMBODIMENTS

Figure 1:
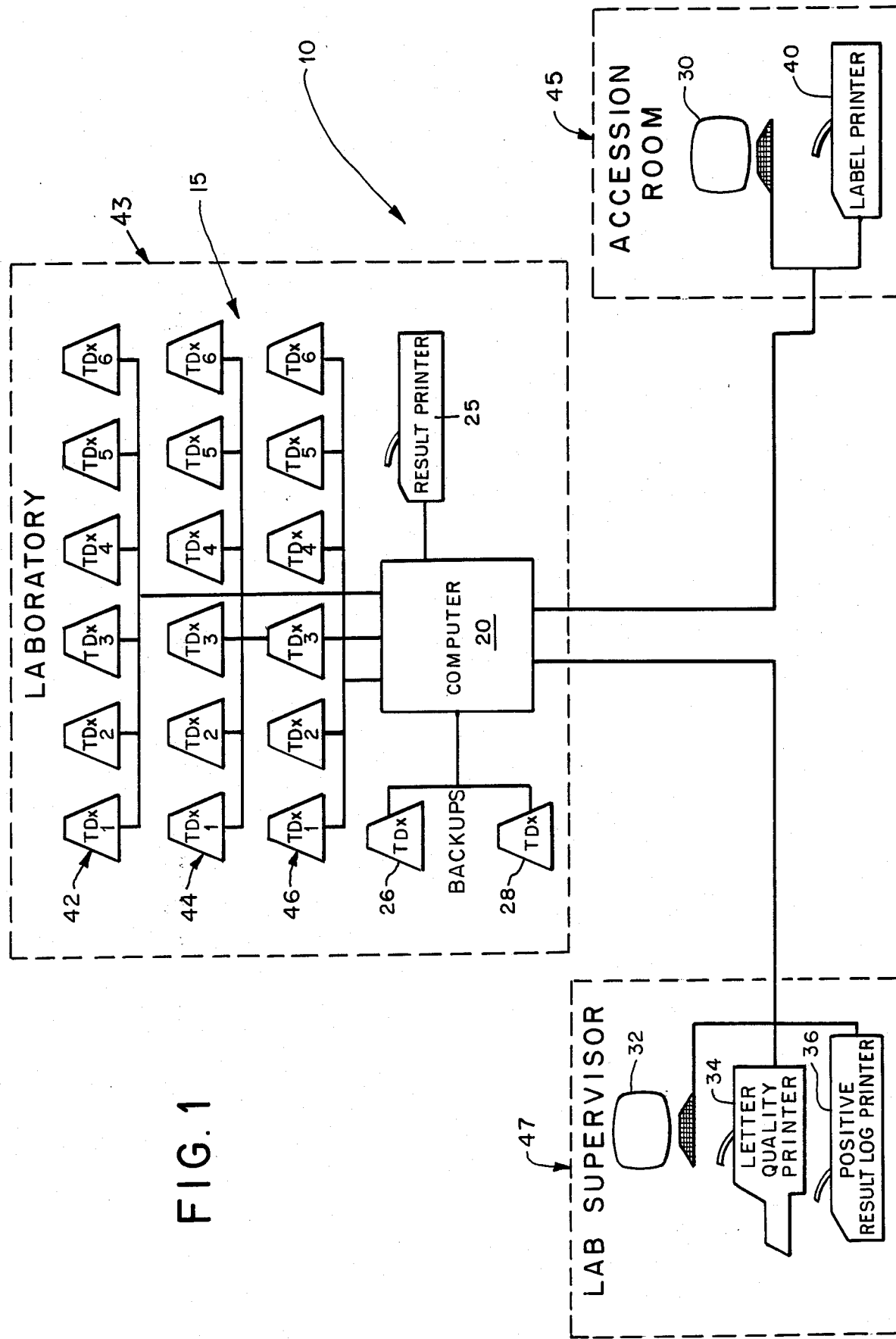
FIG. 1 is a block diagram illustrating generally a typical network of automated clinical analyzers in which the sample containment ring embodying the invention is advantageously employed.
Figure 5:
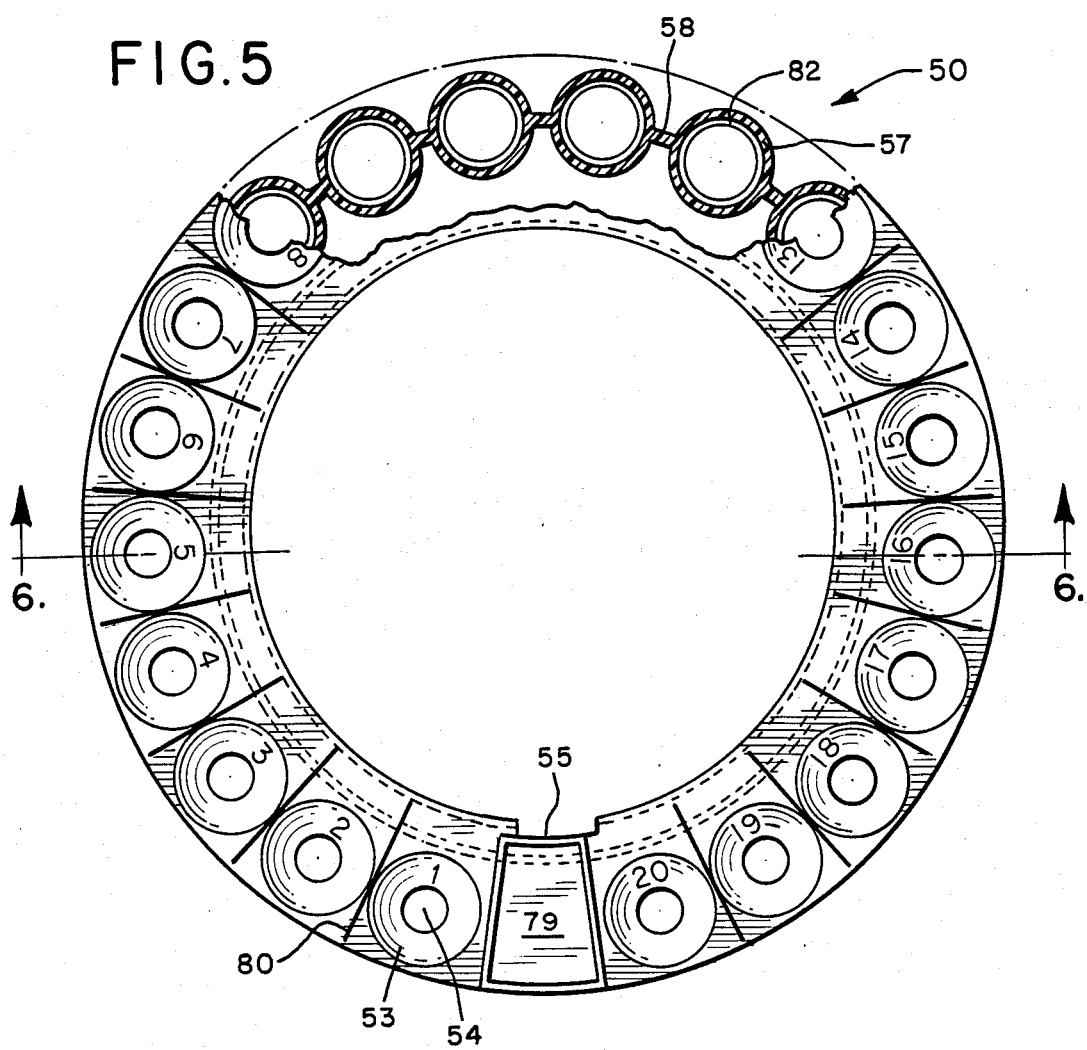
FIG. 5 is a top plan view of the first preferred embodiment of the sample containment ring.

Referring to the drawings, FIG. 1 is a block diagram of an exemplary automated analyzer network 10. The network 10 is comprised of a plurality of clinical analyzers 15, a central computer 20, a result printer 25, backup analyzers 26 and 28, two terminals 30 and 32, a letter quality printer 34, a positive result log printer 36, and a label printer 40. The heart of the network is the central computer 20, which may be a minicomputer such as the MicroVAX/VMS computer manufactured by Digital Equipment Corp. The clinical analyzers 15 are generally microprocessor-controlled analyzers such as the Abbott Laboratories TDx ® Analyzer or similar analyzers. In the exemplary network, the analyzers 15 are grouped in three banks 42, 44, and 46, each having six analyzers 15. Each bank 42, 44 and 46 of analyzers 15 is connected to the central computer 20 by computer networking interfaces and cables so that the microprocessor of each analyzer 15 and the central computer 20 can communicate test results, status information, sample/result correlation data, and sample/test verification data.

The computer 20 is also connected to a pair of backup analyzers 26 and 28 which can be activated as needed to replace other analyzers 15 which are down for repair or other reasons. The computer 20 is also connected to and controls the result printer 25, which is suitably a conventional dot matrix printer, to provide a printed record of the results of tests carried out by the analyzers 15. In the exemplary netword 10, the computer 20, analyzers 15, 26, and 28, and result printer 25 are located in a test laboratory 43.

The computer 20 is also connected by cable to the terminal 30 and label printer 40, which are located in a separate accession room 44, which may be an area off the main laboratory 43, or an entirely separate room or office. The terminal 30 is typically a so-called dumb terminal or work station which is used to input sample and test identification data to the computer 20 for each sample to be tested. The computer 20 controls the label printer 40 to generate accession code labels which are affixed to and travel with the samples as they are tested by the analyzers 15. The accession code labels generated by the printer 40 typically contain optical bar codes which may be read by conventional optical code reading apparatus. Such apparatus is utilized in many known automated analyzers such as the Abbot TDx ® Analyzer, for example.

The computer 20 is also connected to terminal 32, letter quality printer 34, and positive result log printer 36, which in the exemplary network 10 are located in a separate supervisory room or area 47. The terminal 32, which like terminal 30 may be a so-called dumb terminal or work station, allows a laboratory supervisor to monitor the status of the network 10, and provides the supervisor with access to and the ability to control the network 10 through the computer 20. For example, if an analyzer 15 in one of the banks 42, 44 and 46 goes down, the supervisor can instruct the computer 20 to bring one of the backup analyzers 26 and 28 on-line to replace the down analyzer 15. The positive result log printer 36, which may be a dot matrix printer for example, is provided to record only positive tests as reported by the analyzers 15 to the computer 20. The positive result log printer 36 provides the supervisor with ready access to positive result information as well as identifying the persons who tested positive. The letter quality printer 34 can be used by the supervisor for generating reports of test results, system performance, or the like. Alternatively, the functions of both printers 34 and 36 may be performed by a single printer with letter quality capability.

For purposes of describing an exemplary mode of operation of the network 10, it will be assumed that the network 10 is set up in a commercial laboratory to perform high throughput drug testing of samples from different sources such as clinics, law enforcement agencies, private employers, and the like. Typically, biological samples such as serum, urine, or the like, are received and sorted with respect to the tests to be run thereon. The sorted samples are then brought to the accession room 44. In the accession room 44, an operator prepares the samples for testing by transferring all or a portion of each sample from the container it was received in to sample containers which are suitable for mounting on a carousel of an automatic analyzer 15. Each sample container contains an aliquot of a particular sample sufficient to perform a complete battery of selected tests thereon. Each sample has associated with it an identifying number, such as a social security number, which is assigned by the sender of the sample. The operator uses the terminal 30 to enter into the computer 20 the sample identifying number and a corresponding accession code for each sample container and can be used to instruct the computer 20 which test or tests are to be run on each container. The computer 20 stores the assigned accession code for each sample container together with the identifying number of the sample and the test information and causes the label printer 40 to print a label typically containing an optical code which contains the accession code. The operator affixes the appropriate printed label to each sample container.

The prepared sample containers are then carried from the accession room 44 to the laboratory 43 to be tested. In the laboratory 43, each bank 42, 44, and 46 of analyzers 15 may be set up to perform a different or the same battery of tests. Within each bank 42, 44, and 46, each analyzer 15 is set up and optimized to perform a single test which is complimentary to but different from the tests which the other analyzers 15 in the same bank 42, 44, and 46 are set up to perform. For example, the analyzers of bank 46 may be set up to perform drug tests such that one analyzer 15 tests for cocaine, another for amphetamines, another for barbituates, another for marijuana, and so forth. The analyzers 15 in bank 44 may be set up to perform the same or different drug tests, or may be set up to perform entirely different tests such as for herpes, syphilis, AIDS, and other similar viruses. The analyzers 15 in bank 42 may be set up to perform either of the above batteries of tests, or may be set up to perform an entirrely different battery of tests.

In the laboratory 43, each batch of prepared sample containers is loaded in groups onto the carousels of one or more analyzers 15 of the bank 42, 44, and 46 set up for the battery of tests to be performed on the batch. Before each group is tested, the analyzer 15 reads a group identification code and communicates it to the computer 20. The computer 20 responds whether the test is appropriate for the group and if it is, the analyzer 15 performs the test. Otherwise it does not perform the test. After the analyzer 15 reads the result of each test, it communicates the result together with the accession code for the sample to the computer 20. The computer 20 then prints the test result data together with the accession code for the sample on the result printer 25 for the information of a laboratory technician. The computer 20 also prints the accession code and identifying number for each positive test on the positive result log printer 36 for the laboratory supervisor. When an analyzer 15 has completed its test of every sample in the group, it signals the completion to the computer 20, which maintains a record of which tests have been performed on each group identification code. A laboratory technician then unloads the sample containers from the carousel, carries them to the next appropriate analyzer 15, and mounts them onto the carousel. This procedure continues for each group of samples until the entire batch has been tested by all or a selected number of analyzers 15 in the bank 42, 44, and 46. When the complete battery of tests for each sample of a batch has been completed, the lab supervisor can generate a report of the test results for each sample by the identifying number thereof using the terminal 32 and printer 34. The report is then sent to the source of the samples.

Desirably, multiple groups of samples are tested simultaneously by the same bank 42, 44, and 46 of analyzers 15. For example, as the sixth analyzer 15 of a bank 42, 44 and 46 is testing a group of samples for amphetamines, the fifth analyzer 15 can be testing another group for barbituates, the fourth can be testing another group for cocaine, and so on. Also desirably, at the same time one batch, i.e., a plurality of groups, is being tested by one bank 42, 44 and 46 of analyzers 15, another batch is simultaneously being tested by another bank 42, 44, and 46 for the same or different analytes as described above. The sequence of operations and scheduling of the analyzer network 10 is monitored and controlled by the computer 20. At any time, the lab supervisor can gain access to the system status or may alter the system processing from the terminal 32. Thus, for example, if an analyzer 15 in bank 46 should go down, the supervisor can instruct the computer 20 to bring one of the backup analyzers 26 or 28 on line in place of the down analyzer 15.

It should be apparent from the foregoing description of an exemplary mode of operation that the exemplary analyzer network 10 is capable of simultaneously processing a large number of samples rapidly and cost effectively. The high throughput of the network 10 results in lower per sample costs for each test and in overall improved response times. The sample containment apparatus of the invention is intended to further enhance the throughput and cost effectiveness of analyzer networks 10 of the foregoing type by providing means which expedite the sample filling and transfer processes, as well as providing other features and advantages.

Referring to FIG. 2, a first preferred embodiment of a sample containment apparatus of the invention is illustrated in the form of a sample ring 50 which is shown together with a conventional analyzer carousel 60 and diluent ring 70. Generally, the preferred sample ring 50 contains a plurality of sample container means, each adapted to contain a sufficient volume of sample for performing a plurality of tests. The sample ring 50 also contains means for mounting the ring 50 as a unitary structure on the analyzer carousel 60 such that the sample container means are arranged around the periphery thereof. The carousel 60 as illustrated is a known carousel of the type commonly utilized in the well-known Abbott TDx ® Analyzer and is understood to be representative of all analyzer carousels containing the same general structural elements. The diluent ring 70 is a known structure which is adapted to contain a plurality of aliquots of diluent, which are utilized in some tests, and which typically mounts within the carousel 60 as described below.

The critical structural elements of the carousel 60 insofar as the preferred embodiments of the invention are concerned include ring support means, a plurality of reaction container holding means, and key means. As shown in FIGS. 2 and 3, the carousel 60 includes an upper cylindrical section 64 mounted on a base 64a. The ring support means is comprised of a first circular platform 61 which is formed atop the upper cylindrical section 64. The reaction container holding means are comprised of a plurality of cylindrical wells 72 which are vertically formed in the upper cylindrical section 64 and which extend through the top of the first platform 61. In the typical carousel utilized in the Abbott TDx ® Analyzer, for example, twenty such wells are arranged radially around the carousel 60. A second circular platform 63 including a raised key 73 having vertical walls 73a is formed atop the first platform 61. The key 73 comprises the key means. The top surface of the platform 63 is provided with numeric indicia (not shown) corresponding to and identifying each of the reaction container wells 72. The area of the first platform 61 on which the raised key 73 is formed does not include a reaction container well 72 and comprises a reference position for an analyzer.

The carousel also has means for receiving the diluent ring 70. The vertical inner surface of the upper cylindrical section 64 forms an open cylindrical area 75 within the carousel 60. The area 75 is bounded by a circular, horizontal bottom surface 74. A vertically extending cylindrical handle 68 is mounted or attached concentrically to the surface 74. Vertical alignment rods 76, 77, and 78 are formed, embedded, molded, or otherwise attached to the inside surface of the upper cylindrical section 64 at third points of the inside circumference of the cylindrical section 64.

As best illustrated in FIGS. 2 through 6, sample ring 50 comprises an upper ring 52 and a lower ring 52a. The lower ring 52a is comprised of a plurality of interconnected sample containers or cups 57. The upper ring 52 has a flat surface 59 which has formed therein a plurality of frusto-conical funnels 53, each having an opening 54 in the center thereof. Each opening 54 is preferably dimensioned to provide expedient filling of a corresponding sample container 57 while being small enough to restrict the escape of sample if the ring 50 is jostled or otherwise upset. The funnels 53 and corresponding openings 54 are arranged uniformly and radially around the upper ring 52 except for one solid area 79 which has no funnel or opening. As FIG. 10 illustrates, the funnels preferably contain an overhang 122 which surrounds the corresponding opening and which, once sample has been placed in the sample container means, prevents the sample container means from being completely emptied so that the sample containment apparatus cannot be reused. This solid area 79 is provided for receiving a coded label which may contain a group identification code, for example, which is advantageously used to record which tests have been performed on the group of samples of the ring 50, as described above, or to provide other information which it is desirable to have travel with the ring 50. The number and spacing of the funnels 53 and corresponding openings 54 correspond to the number and spacing of the reaction container receiving wells 72 of the carousel 60. In the preferred embodiment, the ring 50 is adapted for use with the typical Abbott TDx ® carousel and therefore contains twenty funnels 53 and corresponding openings 54.

A radially extending vertical rib or barrier 80 is formed on the surface 59 between each funnel 53 to prevent contamination of a sample by spillage or overflow of samples from adjacent funnels 53. First and second vertical circular flanges 56 and 56a respectively are provided on the upper ring 52 for mounting the sample ring 50 on the carousel 60. The flanges 56 and 56a are preferably formed integrally with the upper ring 52 and extend perpendicularly downward from the underside of the surface 59. The flange 56a is preferably formed along the inside edge of the upper ring 52. The flange 56 is preferably separated from the flange 56a by a sufficient distance so that when the sample ring 50 is mounted on the carousel 60 the flange 56a rests on top of the first platform 61 and the flange 56 abuts the outer surface of the upper cylindrical section 64 of the carousel 60 to provide accurate and secure seating of the sample ring 50. The flange 56a preferably has a vertical dimension approximately the same as the height of the second platform 63 and the vertical walls 73a of the raised key 73, and sufficient to ensure secure seating and restriction against radial movement of the ring 50. The flange 56 preferably has a vertical dimension sufficient to engage the outer surface of the upper cylindrical section 64.

The lower ring 52a comprises a plurality of sample containers or cups 57 interconnected in a ring by curved vertical connecting walls 58. Each container preferably has sufficient capacity to contain an aliquot of sample adequate for performing multiple selected tests. Referring to the above-described network 10, for example, each sample container 57 should have sufficient capacity to contain a volume of sample adequate for one test by each of the six analyzers 15 in a bank 42, 44, and 46. The upper and low rings 52 and 52a are preferably concentric and the sample containers 57 are preferably spaced around the lower ring 52a such that when the rings are connected, each container is concentric with and positioned immediately below an opening 54 of the upper ring 52. In the preferred embodiment, the lower ring 52a comprises twenty-one sample containers 57, twenty of which correspond to openings 54 of the preferred upper ring 52 and one of which is covered by the area 79.

Figure 6:
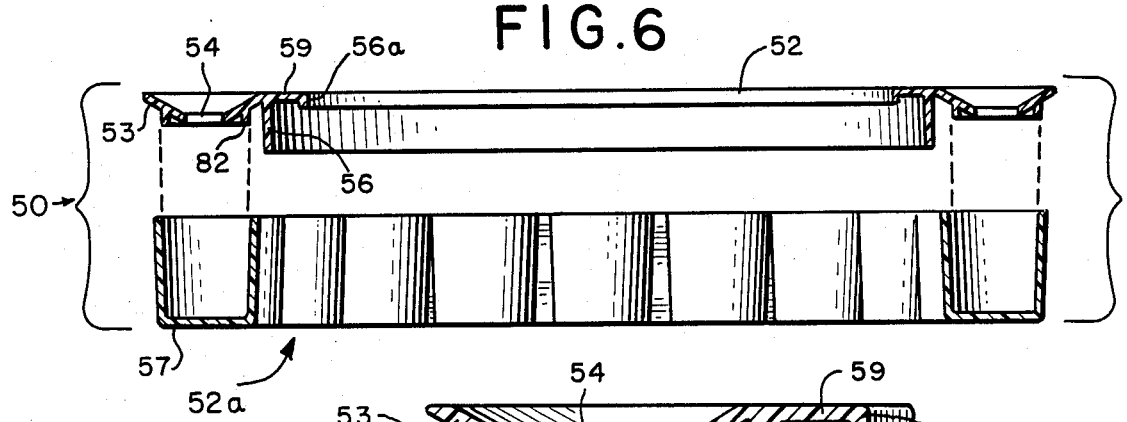
FIG. 6 is an exploded side elevation view in section of the sample containment ring of FIG. 5, taken along a line 6—6.
Figure 7:
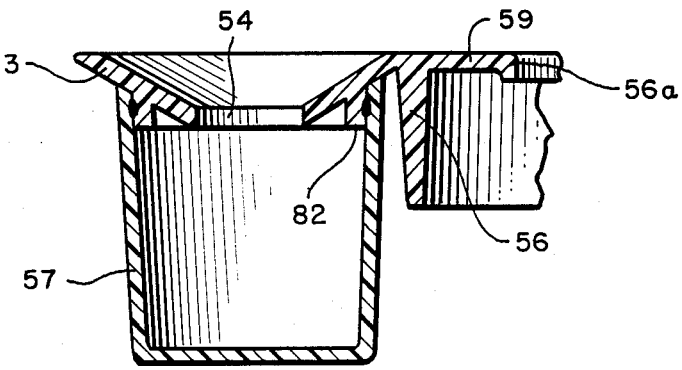
FIG. 7 is an enlarged side elevation view in section of the sample containment ring of FIG. 6 illustrating the mating relationship between a representative funnel portion of the upper ring and a corresponding representative sample container portion of the lower ring.

For reasons of economy, it is preferred that the top and bottom rings 52 and 52a be manufactured separately of a suitable plastic material such as ABS or SAN plastic using conventional plastic molding techniques. The rings 52 and 52a are then connected to form a unitary fluid-tight sample containment apparatus or ring 50. As best illustrated in FIGS. 6 and 7, the underside of each funnel 53 includes a vertically projecting circular flange 82. The flange 82 has an outside diameter related to the inside diameter of the sample containers 57 such that the flange 82 fits flush within a corresponding sample container 57 in a secure press fit with the inside surface thereof. To further ensure a secure, fluid-tight connection between the upper and lower rings 52 and 52a, the top edges of each of the containers 57 are preferably angled at approximately the same angle as the conical sides of the funnels 52 which they abut when the two rings 52 and 52a are connected. To still further ensure a secure, fluid-tight connection between the upper and lower rings 52 and 52a, it is preferred that the two be welded together, preferably by ultrasonic welding, or another similar technique capable of providing secure, fluid-tight connection between the two rings.

As best illustrated in FIGS. 2 and 4, ring alignment means are provided on the upper ring 52 in the form of a notch 55 formed adjacent to the solid area 79. The notch 55 is dimensioned to receive and engage vertical walls 73a of the raised key 73 of the carousel 60 in locking or abutting relationship when the sample ring 50 is mounted on the carousel 60. The notch 55 is preferably positioned in the upper ring 52 such that when the sample ring 50 is mounted on the carousel 60, the center of each opening 54 and each underlying sample container 57 of the ring 50 is adjacent to and aligned along an arcuate path with the center of a corresponding reaction container receiving well 72 of the carousel 60. The arcuate relationship of the openings 54 and wells 72 is preferred to facilitate access by a radially pivoting mechanical arm and associated pipetting means of the type used in analyzers such as the Abbott TDx ® Analyzer. Alternatively, other alignment relationships such as linear alignment may be provided by repositioning the notch 55 relative to the key 73 as required for other arrangements of mechanical arms and pipetting means in other analyzers. The locking relationship of the raised key 73 and notch 55 prevent rotational motion of the sample ring 50 from the desired position once it is mounted on the carousel 60.

Because the preferred sample ring 50 mounts around the periphery of the carousel 60, it provides access to the carousel 60 for an additional diluent-containing ring such as ring 70 to be mounted if necessary or desirable for certain tests. The diluent ring 70 illustrated is similar to other known diluent rings. The diluent ring 70 generally comprises an inner cylindrical wall 85 which is connected to an outer concentric cylindrical wall 88 by a plurality of radially extending, uniformly spaced dividing walls 84. The dividing walls 84, together with the bottom (not shown) and inner and outer walls 85 and 88 form a plurality of diluent chambers. In the diluent ring 70 adapted for the Abbott TDx ® Analyzer, for example, twenty-one such chambers, twenty corresponding to reaction container receiving wells 72 of the carousel 60 and corresponding openings 54 of the preferred sample ring 50 are provided. The inner wall 85 of the ring 70 preferably has a diameter sufficient to mount the ring 70 over the handle 68 within the carousel 60. The diameters of the inner and outer walls 85 and 88 are also preferably selected such that the ring 70 fits within the open area 75 of the carousel 60 with minimal free play between the ring 70 and the carousel 60. At each point along the circumference of the outer wall 88 where a dividing wall 84 intersects the wall 88, the outer wall 88 has formed therein a half-cylindrical alignment or locking receptacle 87, 87. Such receptacle is dimensioned to receive one of the vertical rods 76, 77, or 78 on the inner wall of the upper cylindrical section 64 of the carousel 60 in locking relationship. The locking relationship between the rods 76, 77, and 78 and the receptacles 87 prevent the ring 70 from rotating in the carousel 60 and ensure that each diluent chamber is aligned along the same arcuate path as the corresponding well 72 of the carousel 60 and opening 54 of the preferred sample containment ring 50.

FIGS. 8 through 10 illustrate a second preferred embodiment of the sample containment apparatus of the invention. In the second preferred embodiment, a sample ring 90 is integrally formed of a suitable plastic such as ABS or SAN plastic by conventional plastic molding techniques. Sample ring 90 generally comprises a vertical cylindrical wall 92 and a ring-shaped horizontal support surface 100 which encircles the vertical wall 92 at approximately one-third the distance of its vertical dimension. The vertical wall 92 has a horizontal flange 94 formed around the entire circumference of the top thereof and the flange 94 has a vertical flange 56' formed around its inner periphery for mounting the sample ring 90 on the platform 61 of the carousel 60.

The support surface 100 contains a plurality of openings 96 which are adapted to hold a corresponding plurality of sample containers or cups 104. The openings 96, similarly to the first preferred embodiment are arranged uniformly and radially around the support surface 100 except for one solid area 102. Similarly to the first preferred embodiment, the area 102 is provided for receiving a coded label. Also, a notch 93 similar to the notch 55 of the first preferred embodiment is formed in the lip 94 adjacent to the solid area 102 of the support surface 100 for the same purpose as the notch 55. Vertical support walls 98 formed integrally with the bottom surface of the support surface 100 extend downward and radially outward between each opening 96. The support walls 98 are provided to support the ring 90 on a flat surface to facilitate mounting of sample containers 104 in openings 96 of the ring 90.

In contrast to the first preferred embodiment, each sample container 104 of the second preferred embodiment is manufactured as a separate unit and is adapted to be mounted individually in an opening 96 of the sample ring 90. Each container 104 is preferably manufactured of a suitable plastic such as ABS or SAN plastic by conventional plastic molding techniques. Each container 104 comprises a lower cylindrical portion 106 and an upper cylindrical portion 108. The upper cylindrical portion 108 preferably has a slightly larger diameter than the lower portion 106 so that the junction of the two portions forms a support shoulder 110.

Each container 104 also includes a lid 114 which can be molded integrally with the container 104 and permanently attached thereto by a connector. The connector which is illustrated in FIG. 12 prevents the loss of the lid 114 or possible contamination of a sample by the inadvertent use of a lid 114 from another container 104. Alternatively the lid 114 and container 104 can be molded separately and assembled as a unit.

Each lid 114 is comprised of an upper cylindrical portion 116 and a lower cylindrical portion 118. The upper cylindrical portion 116 preferably has a slightly larger diameter than the lower cylindrical portion 118 so that at the junction of the two portions a support shoulder 120 is formed. A frusto-conical funnel 122 is preferably integrally formed inside each lid 114 between the inside walls of the upper cylindrical portion 116. An opening 124 is provided in the center of each funnel 122 to provide a fluid passage into the container 104. The top of the funnel 122 is preferably positioned below the top of the wall of the upper cylindrical portion 116 so that a portion of the vertical wall forms a barrier which encircles the funnel 122 and prevents spillage during filling of the sample container 104. The opening 124 is preferably dimensioned to provide expedient filling of the sample container 104 while being small enough to restrict the escape of sample from the container 104 if it is jostled or otherwise upset.

As best illustrated in FIG. 10, the flange 56' of the sample ring 90 rests on the surface of the first raised platform 61 of the carousel 60 when the ring 90 is mounted on the carousel 60. The flange 56' and vertical wall 92 of the ring 90 are separated by the flange 94 so that the wall 92 abuts the outside surface of the upper cylindrical portion 64 of the carousel 60 to provide accurate and secure mounting of the ring 90 around the periphery of the carousel 60.

Also as shown in FIG. 10, the support shoulder 110 of each container 104 preferably rests on and is supported by the support surface 100 of the sample ring 90 when the container 104 is mounted in an opening 96. Preferably, the upper and lower cylindrical portions 108 and 106 of the container 104 are dimensioned to provide a wide enough shoulder 110 to eliminate the possibility of the container slipping through an opening 96. The vertical wall of the upper cylindrical portion 108 of each container 104 is elevated above the surface 100 and acts as a barrier which prevents spillage of sample from one container 104 from entering another container 104 and contaminating the sample therein.

Also as shown in FIG. 10, the lower cylindrical portion 118 of the lid 114 preferably fits flush with and forms a secure press fit with the inside wall of the upper cylindrical portion 108 of the container 104 when the lid 114 is mounted thereon. The shoulder 120 of the lid 114 rests upon the top of the upper cylindrical section 108 of the container 104 to form a secure fluid-tight connection therewith when the lid 114 is mounted thereon. In addition, the diameter of the upper cylindrical portion 108 of the lid 114 is preferably dimensioned to provide a support shoulder 120 which is wide enough to prevent slippage of the lid 114 into the container 104.

Although not illustrated and not required, it may be desirable in some instances to provide locking tabs on the outside wall of the lower cylindrical portion 106 of each container 104 to prevent removal of the container 104 once it is mounted in an opening 96 of the sample ring 90. If desired, the locking tabs could be provided with a means for unlocking so that only inadvertent removal of the containers 104 is prevented.

Figure 11:
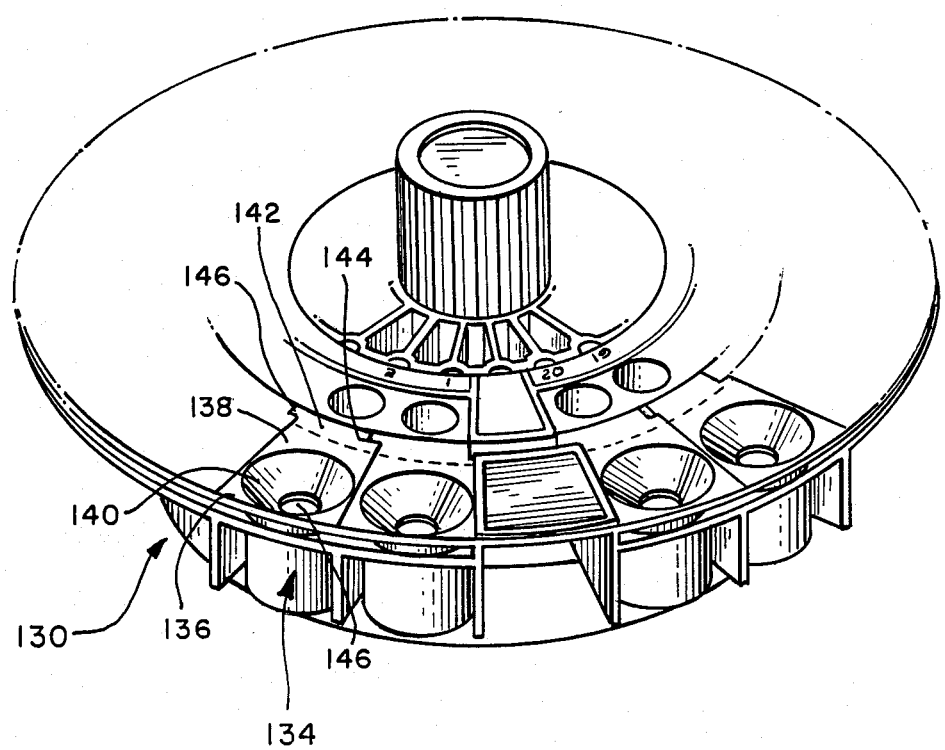
FIG. 11 is a partial front perspective view of a third preferred embodiment of the sample containment ring and sample containers shown mounted therein.

FIG. 11 illustrates a third preferred embodiment of the sample containment apparatus of the invention. This embodiment includes a sample containment ring 130 and separate sample containers 134 mountable in the ring 130. The sample containment ring 130 is essentially similar to the sample containment ring 90 of FIG. 8. The sample containers 134 are essentially similar to sample container 104 illustrated in FIG. 9. Each sample container 134 has a lid 136. The lid 136 is essentially similar to the lid 114 illustrated in FIG. 9, except that the lid 136 includes an extended horizontal mounting surface 138. The mounting surface 138 extends outwardly from the top of a funnel 140 in the lid 136 and has a lateral dimension that converges toward the center of the carousel 60 to allow a plurality of containers 134 to be mounted on the ring 130 around the periphery of the carousel 60. At the inner periphery of each mounting surface 138 is an area 142 provided for receiving a coded label or a molded code, such as a bar code, which can be advantageously used to identify each sample. Preferably, each surface 138 has a notch 144 on a first side and a tab 146' on a second side of its inner periphery to provide offset mounting of the containers 134 on the ring 130 so that central openings 146 of the funnels 140 are maintained along an arcuate path with reaction container openings 54 on the carousel 60 as described above. The relationship between the lid 136, sample container 134, and ring 130 is essentially the same as shown with respect to the lid 114, container 104, and ring 90 in FIG. 10.

Certain advantages and features provided by the preferred sample rings 50, 90, and 130 embodying the invention will now be described with reference to the previous description of exemplary operation of the analyzer network 10. In the accession room 44, an operator fills each of the sample containers of a preferred sample ring with an aliquot of sample sufficient to supply adequate sample for the entire battery of tests to be run by the selected bank of analyzers. The operator is required to fill and prepare only one container rather than multiple containers for each sample to be tested. The sample containers of the first preferred embodiment form an integral unit with the sample ring and may be filled either individually by an operator or automatically by automatic filling equipment. The containers of the second and third preferred embodiments may also be preloaded into the sample ring and filled manually by the operator or automatically by automated filling equipment. In addition, since the cups of the second and third preferred embodiments are not integral with the ring, these embodiments provide an additional feature in that the samples can be individually taken directly in the containers at the testing facility itself and delivered to the accession room for labelling and mounting in the sample ring for testing. Also, since the containers of the second and third preferred embodiments comprise separate units, they can be filled remotely from each other which minimizes the chance of cross-contamination between samples.

The funnels in each of the embodiments expedite the filling process and prevent spillage. In the first preferred embodiment, the radial ribs between each funnel prevent the accidental spillage or overflow of sample from one container into adjacent containers. In the second and third preferred embodiments, the raised vertical walls of the upper cylindrical portions of the containers perform the same function.

Once each of the containers of a group of samples are filled and labelled with an accession code, the entire group is expediently carried by way of the sample ring to an analyzer of the appropriate bank for testing. The relatively small diameter of the openings for filling the containers in each embodiment prevent spillage or leakage during transit of the sample ring and during loading and unloading of the sample ring to and from the analyzers. In addition, since each sample container is mounted or integrally formed in a specific position of the ring, the risk of inadvertent switching of positions of the samples is prevented.

The key-receiving notch on each ring cooperates with the raised key on the carousel of each analyzer to ensure that the sample ring is mounted in each analyzer with the sample containers properly aligned with corresponding reaction containers of the carousel and in the same relative positions with respect to each analyzer. Further, the top surface of the solid area on each ring adjacent to the notch provides a convenient location for placement of a ring or group identifying label.

When an analyzer completes the testing of the entire group of samples mounted on a sample ring, the operator expeditiously transfers all of the samples of the batch simultaneously and in fixed position to the next analyzer by simply removing the sample ring from the analyzer carousel, carrying it to the next analyzer, and mounting it on the carousel for that analyzer. There is no need for the technician to refill sample containers or to ensure that containers for the current test are in the same positions as for the previous test(s). As a result, sample preparation time and the time between tests are reduced, system throughput is improved, and the possibility of interposition and contamination of the samples is minimized. It will also be appreciated that a sample ring according to the invention can be advantageously used to facilitate the handling of samples with stand-alone analyzers.

Since each sample ring mounts around the periphery of a carousel, a diluent ring can also be mounted on the inside of the carousel if required by specific analyzers which are set up to perform tests that require dilution of the samples. When the entire battery of tests have been performed on a group of samples on a sample ring, the sample containers, together with the sample ring may be disposed of to prevent future sample contamination that may occur through re-use. Alternatively, although not intended by the preferred embodiment, the second and third preferred embodiments can provide the ability to remove the used sample containers while retaining the sample ring itself for future use.

In each of the preferred embodiments 50, 90, and 130 of the ring, an insert (not shown) can be provided in a selected position of the ring which contains a reduced volume of sample needed for calibration, controls, or standards of the analyzer, or where smaller volumes of specimen samples are desired.

What have been described are certain aspects of sample containment rings for use in automated clinical analyzer networks which constitute the presently preferred embodiments of the invention. It is understood that the foregoing detailed description and accompanying illustrations are merely exemplary and are not to be taken as limiting the scope of the invention, which is defined solely by the appended claims and their equivalents. Various changes and modifications to the preferred embodiments will be apparent to those skilled in the art. Such changes and modifications, including without limitations, changes to the dimensions, appearance, materials, shape, and form of the preferred embodiments and various components thereof may be made without departing from the spirit and scope of the invention. Accordingly, it is intended that all such changes and modifications be covered by the appended claims and their equivalents.

We claim:

1. A sample containment apparatus for use in an automated analyzer network comprising a plurality of analyzers, each of said analyzers being operative to perform a selected test on a plurality of samples, and each of said analyzers including a carousel having a plurality of reaction container holding means, comprising:
   ring means having a plurality of openings for receiving a plurality of samples to be tested, said ring means including a plurality of funnel means, each of said funnel means being formed around each of said corresponding openings in said plurality of openings;
   a plurality of radially extending rib means located on said ring means between adjacent openings to prevent contamination of one sample by spillage from another;
   a plurality of sample container means; and
   mounting means attached to said ring means for removably mounting said sample containment apparatus on each carousel of a selected number of analyzers in an automated analyzer network.

2. A sample containment apparatus for use in an automated analyzer network comprising a plurality of analyzers, each of said analyzers being operative to perform a selected test on a plurality of samples, and each of said analyzers including a carousel having a plurality of reaction container holding means, comprising:
   ring means having a plurality of openings for holding a plurality of sample container means;
   a plurality of sample container means mountable in said plurality of openings for containing a plurality of samples to be tested;
   a corresponding plurality of cap means mountable on said sample container means for closing said sample container means; and
   mounting means attached to said ring means for removably mounting said sample containment apparatus on each carousel of a selected number of analyzers in an automated analyzer network to perform a selected plurality of tests on said plurality of samples;
   said mounting means comprising a horizontal flange formed around the circumference of the top of a vertical wall included on said ring means, said horizontal flange having a vertical flange formed around its inner periphery, said vertical flange being adapted to rest on the surface of a first raised platform of one of said carousels when said ring means is removably mounted on one of said carousels.

3. A sample containment apparatus for use in an automated analyzer network comprising a plurality of analyzers, each of said analyzers being operative to perform a selected test on a plurality of samples, and each of said analyzers including a carousel having a plurality of reaction container holding means, comprising:
   ring means having a plurality of openings for holding a plurality of sample container means;
   a plurality of sample container means mountable in said plurality of openings for containing a plurality of samples to be tested;
   a corresponding plurality of cap means mountable on said sample container means for closing said sample container means;
   each of said cap means including an opening for receiving sample when said cap means is mounted to said sample container means; and
   mounting means attached to said ring means for removably mounting said sample containment apparatus on each carousel of a selected number of analyzers in an automated analyzer network to perform a selected plurality of tests on said plurality of samples.

4. The apparatus defined in claim 3 wherein each of said cap means further includes a funnel means formed around said opening for facilitating the introduction of said sample into said sample container means.

5. The apparatus defined in claim 4 wherein each of said funnel means includes an overhang disposed around each of said corresponding openings in said plurality of openings and which, once sample has been placed in said sample container means, impairs said sample container means from being completely emptied so that said sample containment apparatus cannot be reused.

6. The apparatus defined in claim 5 wherein said overhang extends inwardly towards the center of said sample container means forming said openings.

7. A sample containment apparatus for use in an automated analyzer network comprising a plurality of analyzers, each of said analyzers being operative to perform a selected test on a plurality of samples, and each of said analyzers including a carousel having a plurality of reaction container holding means, comprising:
   ring means having a plurality of openings for holding a plurality of sample container means;
   a plurality of sample container means mountable in said plurality of openings for containing a plurality of samples to be tested;
   one or more of said sample container means including one or more inserts;
   a corresponding plurality of cap means mountable on said sample container means for closing said sample container means; and
   mounting means attached to said ring means for removably mounting said sample containment apparatus on each carousel of a selected number of analyzers in an automated analyzer network to perform a selected plurality of tests on said plurality of samples.

8. A sample containment apparatus for use in an automated analyzer network comprising a plurality of analyzers, each of said analyzers beng operative to perform a selected test on a plurality of samples, and each of said analyzers including a carousel having a plurality of reaction container holding means, comprising:
   ring means having a plurality of openings for holding a plurality of sample container means;
   a plurality of sample container means mountable in said plurality of openings for containing a plurality of samples to be tested;
   a corresponding plurality of cap means mountable on said sample container means for closing said sample container means;
   said cap means including a horizontal mounting surface which extends outwardly from the top of said cap means towrds the center of said carousels; and
   mounting means attached to said ring means for removably mounting said sample containent apparatus on each carousel of a selected number of analyzers in an automated analyzer network to perform a selected plurality of tests on said plurality of samples.

9. A sample containment apparatus for use in an automated analyzer network comprising a plurality of analyzers, each of said analyzers being operative to perform a selected test on a plurality of samples, and each of said analyzers including a carousel having a plurality of reaction container holding means, comprising:

ring means having a plurality of openings for holding a plurality of sample container means;

a plurality of sample container means mountable in said plurality of openings for containing a plurality of samples to be tested;

a corresponding plurality of cap means mountable on said sample container means for closing said sample container means; said cap means including a horizontal mounting surface which extends outwardly from the top of said cap means towards the center of said carousels;

connecting means for connecting each of said cap means to a corresponding sample container means; and mounting means attached to said ring means for removably mounting said sample containment apparatus on each carousel of a selected number of analyzers in an automated analyzer network to perform a selected plurality of tests on said plurality of samples.

10. A sample containment apparatus for use in an automated analyzer network comprising a plurality of analyzers, each of said analyzers being operative to perform a selected test on a plurality of samples, and each of said analyzers including a carousel having a plurality of reaction container holding means, comprising:

ring means having a plurality of openings for holding a plurality of sample container means removably mounted on one of said carousels, said ring means including a vertical wall, a horizontal flange formed around the circumference of the top of said vertical wall, and an alignment means for being engaged by a corresponding means of said carousels for mounting said sample containment apparatus on one of said carousels with a predetermined orientation, said alignment means comprising a notch which is formed in said horizontal flange;

a plurality of sample container means mountable in said plurality of openings for containing a plurality of samples to be tested;

a corresponding plurality of cap means mountable on said sample container means for closing said sample container means; and mounting means attached to said ring means for removably mounting said sample containment apparatus on each carousel of a selected number of analyzers in an automated analyzer network to perform a selected plurality of tests on said plurality of samples.

11. A sample containment apparatus for use in an automated analyzer network comprising a plurality of analyzers, each of said analyzers being operative to perform a selected test on a plurality of samples, and each of said analyzers including a carousel having a plurality of reaction container holding means, comprising:

ring means having a plurality of openings for receiving a plurality of samples to be tested, said ring means including a plurality of funnel means, each of said funnel means being formed around each of said corresponding openings in said plurality of openings, and;

each of said funnel means including an overhang disposed around each of said corresponding openings in said plurality of openings and which, once sample has been placed in said sample container means, impairs said sample container means from being completely emptied so that said sample containment apparatus cannot be reused;

a plurality a sample container means; and mounting means attached to said ring means for removably mounting said sample containment apparatus on each carousel of a selected number of analyzers in an automated analyzer network.

12. The apparatus defined in claim 11 wherein said overhang extends inwardly towards the center of said sample container means forming said openings.

13. A sample containment apparatus for use in an automated analyzer network comprising a plurality of analyzers, each of said analyzers being operative to perform a selected test on a plurality of samples, and each of said analyzers including a carousel having a plurality of reaction container holding means, comprising:

ring means having a plurality of openings for receiving a plurality of samples to be tested, said ring means including a plurality of funnel means, each of said funnel means being formed around each of said corresponding openings in said plurality of openings, and said ring means including a vertical wall, a horizontal flange formed around the circumference of the top of said vertical wall, and an alignment means for being engaged by a corresponding means of said carousels for mounting said sample containment apparatus on one of said carousels with a predetermined orientation, said alignment means comprising a notch which is formed in said horizontal flange;

a plurality of sample container means; and mounting means attached to said ring means for removably mountng said sample containment apparatus on each carousel of a selected number of analyzers in an automated analyzer network.

14. The apparatus defined in claim 13 wherein said ring means is removably mounted on one of said carousels.

15. The apparatus defined in claim 14 wherein said carousel is attached to one of said analyzers.

16. The apparatus defined in claim 14 wherein a diluent ring is removably mounted in said carousel.

17. The apparatus defined in claim 15 wherein a diluent ring is removably mounted in said carousel.

18. The apparatus defined in claim 15 wherein said horizontal mounting surface is adapted for receiving identifying indicia.

19. A sample containment apparatus for use in an automated analyzer network comprising a plurality of analyzers, each of said analyzers being operative to perform a selected test on a plurality of samples, and each of said analyzers including a carousel having a plurality of reaction container holding means, comprising:

ring means having a plurality of openings for receiving a plurality of samples to be tested, said ring means including at least one area adapted for receiving identifying indicia and a plurality of funnel means, each of said funnel means being formed around each of said corresponding openings in said plurality of openings;
a plurality of sample container means; and
mounting means attached to said ring means for removably mounting said sample containment apparatus on each carousel of a selected number of analyzers in an automated analyzer network.

20. A sample containment apparatus for use in an automated analyzers network comprising a plurality of analyzers, each of said analyzers being operative to perform a selected test on a plurality of samples, and each of said analyzers including a carousel having a plurality of reaction container holding means, comprising:
   ring means having a plurality of openings for receiving a plurality of samples to be tested, said ring means including a plurality of funnel means, each of said funnel means being formed around each of said corresponding openings in said plurality of openings;
   a plurality of sample container means;
   mounting means attached to said ring means for removably mounting said sample containment apparatus on each carousel of a selected number of analyzers in an automated analyzer network; and
   said apparatus comprising an upper ring which is mounted on a lower ring, said lower ring comprising said plurality of sample container means, said sample container means being interconnected, and said upper ring comprising a flat surface which has formed thereon said plurality of funnel means, said funnel means and said corresponding openings being arranged radially and uniformly around said upper ring except for one area which is adapted for receiving identifying indicia.

* * * * *